United States Patent [19]

Triunfol

[11] Patent Number: 4,744,354

[45] Date of Patent: May 17, 1988

[54] BODY RESTRAINT

[76] Inventor: David Triunfol, 2001 N. 72nd Ct., Elmwood Park, Ill. 60635

[21] Appl. No.: 884,607

[22] Filed: Jul. 11, 1986

[51] Int. Cl.$^4$ .......................... A61F 5/37; A61F 13/00
[52] U.S. Cl. ................................. 128/134; 2/DIG. 7; 2/326
[58] Field of Search ........................... 5/494, 424, 498; 128/133, 134, 135; 2/326, 327, 328, DIG. 7

[56] References Cited

U.S. PATENT DOCUMENTS

| | | | |
|---|---|---|---|
| 2,751,594 | 6/1956 | Brissenden | 2/49 |
| 2,782,783 | 2/1957 | Gay | 128/134 |
| 2,851,033 | 9/1958 | Posey | 128/134 |
| 3,136,311 | 6/1964 | Lewis | 128/134 |
| 3,137,294 | 6/1964 | Robertson | 128/134 |
| 3,181,530 | 5/1965 | Storey | 128/134 |
| 3,259,126 | 7/1966 | Greiert | 128/134 |
| 3,265,065 | 8/1966 | Jillson | 128/134 |
| 3,276,432 | 10/1966 | Murcott | 119/96 |
| 4,050,737 | 9/1977 | Jordan | 297/389 |
| 4,117,840 | 10/1978 | Rasure | 128/134 |
| 4,119,095 | 10/1978 | Lewis | 128/134 |
| 4,488,544 | 12/1984 | Triunfol | 128/134 |
| 4,657,005 | 1/1986 | Williamson | 128/134 |

Primary Examiner—Richard J. Johnson
Attorney, Agent, or Firm—Andrus, Sceales, Starke & Sawall

[57] ABSTRACT

An improved body restraint comprising a vest body having a front panel and a pair of separable back panels. A first strap is connected to the lower edge of each back panel and extends transversely across the vest body and is received within a loop or slot in the other back panel. The ends of the first straps are adapted to be attached to an outside object, such as the side rails of a bed. Second straps are connected to the vest body at locations beneath each arm opening, and each second strap extends diagonally across the vest body and is adapted to be attached to the head rail of the bed. The body restraint will securely restrain a patient and yet the diagonally extending straps permit the patient to move from side-to-side without danger of release. During movement of the patient, tension is concentrated under the arms to eliminate any possibility of stress being concentrated on the neck of the patient.

3 Claims, 1 Drawing Sheet

BODY RESTRAINT

BACKGROUND OF THE INVENTION

In the past, body restraints have been of a type that wrap around the patient's body and are provided with straps at waist level which can be secured to a bed or chair. It has been found that a patient by struggling can sometimes can become released from the restraint, or alternately, will slip down into the restraint to a point where the front panel of the restraint can apply dangerous stress to the throat of the patient.

U.S. Pat. No. 4,488,544 discloses an improved body restraint which more securely restrains a patient and yet is simple to apply. The body restraint of the aforementioned patent includes a body vest composed of a front panel and a pair of overlapping body panels. The lower edge of each back panel is provided with a strap and the strap of each back panel extends transversely across the vest body and is received within a loop or slot in the opposite back panel. The free ends of the straps are adapted to the connected to an outside object, such as the side rails of a bed.

In addition, the body restraint of the aforementioned patent includes a pair of straps which are connected to the free vertical edges of the back panels and the free ends of these straps extend beneath the head of the patient and are adapted to be connected to the top rail of the bed.

SUMMARY OF THE INVENTION

The invention is directed to an improved body restraint which will securely restrain a struggling patient and yet will prevent undue stress being applied to the throat of the patient. In accordance with the invention, the body restraint includes a vest body having a front panel and a pair of separable back panels. A first strap is connected to the lower edge of each back panel and extends transversely across the other back panel and is received within a loop or slot. The free ends of the straps are adapted to be connected to an outside object, such as the side rails of a bed.

In addition, a second strap is connected to each back panel at a location beneath the arm opening, and each second strap extends diagonally upwardly across the back of the vest body and is attached to the head rail of the bed.

With this configuration of straps, the patient is securely held although the arrangement permits limited side-to-side movement. Furthermore, tension caused by struggling of the patient is concentrated under the arms of the patient so that any stress due to the struggling is not concentrated at the neck or throat area of the patient.

The body restraint is of inexpensive construction and can be readily applied to the patient without the use of any auxiliary fasteners, clamps or the like.

Other objects and advantages will appear in the course of the following description.

DESCRIPTION OF THE DRAWINGS

The drawings illustrate the best mode presently contemplated of carrying out the invention.

In the drawings.

DESCRIPTION OF THE ILLUSTRATED EMBODIMENT

Figure 1:
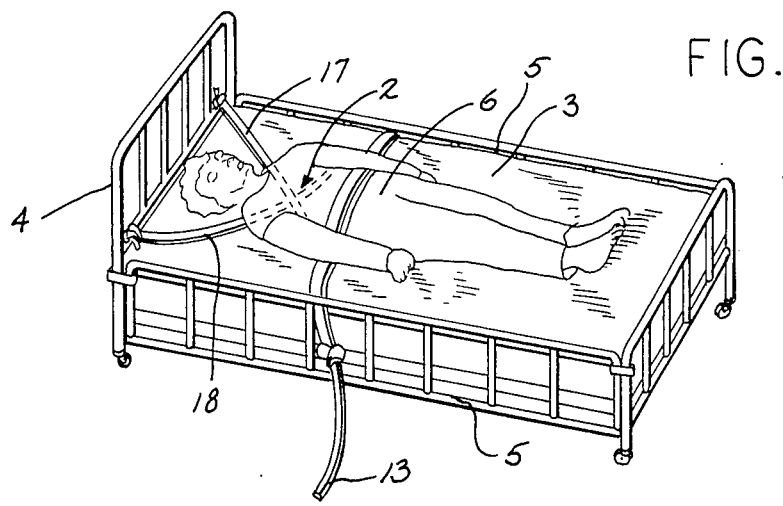
FIG. 1 is a perspective view of a patient fitted with the body restraint of the invention.

The drawings illustrate a body restraint 1 fitted on a patient 2 who is restrained to a bed 3 that includes a head rail 4 and side rails 5. While the drawings illustrate the body restraint used to restrain a patient in bed, it is also contemplated that the restraint can be employed to restrain a patient in a wheelchair, diagnostic table, and the like.

Figure 2:
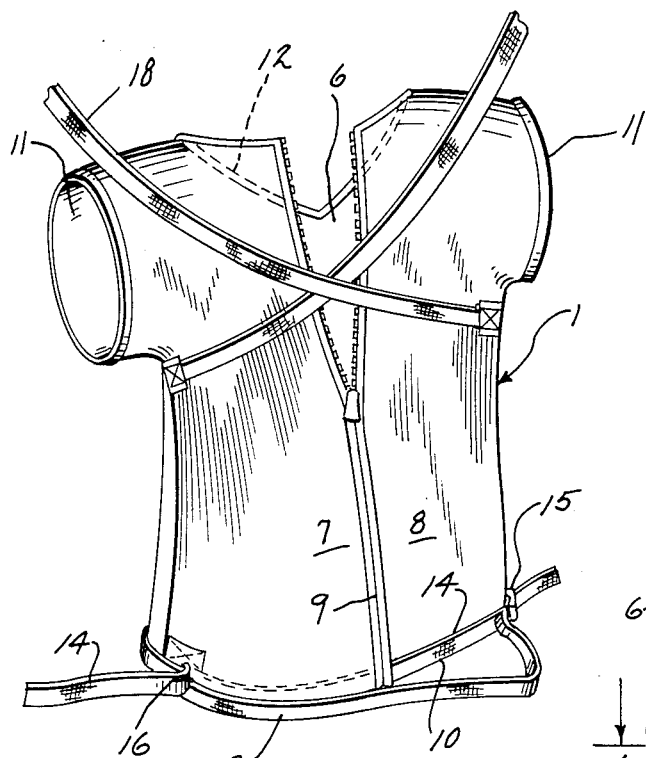
FIG. 2 is an enlarged perspective view of the body restraint as viewed from the back.
Figure 3:
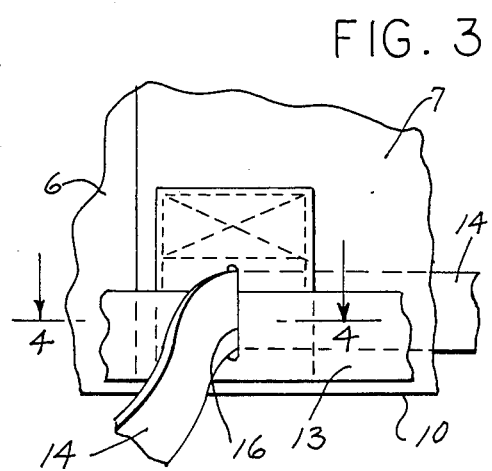
FIG. 3 is an enlarged fragmentary plan view of the vertical slot area.
Figure 4:
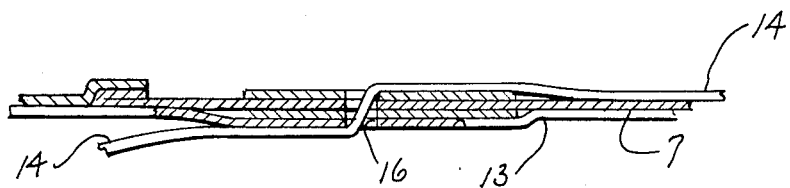
FIG. 4 is a horizontal section taken along line 4—4 of FIG. 3.

Body restraint 1 is formed of a relatively strong fabric material comprising a unitary vest body including a front panel 6 and a pair of back panels 7 and 8 which are joined to the respective sides of the front panel 6. As best shown in FIG. 2, the free vertical edges of back panels 7 and 8 can be connected together by a zipper 9. It is contemplated that other fasteners can be substituted for the zipper 9 and in some cases the free vertical edges of back panels 7 and 8 may merely be disposed in overlapping relation without connectors or fasteners.

The body restraint also includes a lower horizontal edge or waist 10, and the front panel 6 and back panels 7 and 8 define arm openings 11. As best shown by the phantom lines in FIG. 2, the upper edge of front panel 6 has a generally V-shaped neck 12.

Reinforcing straps 13 and 14 are attached by sewing or the like to the lower edge 10 of back panels 7 and 8. Strap 13, which is attached to back panel 7, extends transversely across the lower edge of back panel 8 and is received within a slot or loop 15. Strap 14, which is secured to the lower edge 10 of back panel 8, extends inside of the lower edge of back panel 7 and projects outwardly through a slot 16 formed in the panel 7. Straps 13 and 14 when tightened to the patient are adapted to be tied to an outside object such as the side rails 5 of the bed, as illustrated in FIG. 1.

While the drawings illustrate strap 14 being located on the inside of back panel 7, it is contemplated that the straps 13 and 14 can be offset vertically in which case both straps could be located on the outside of the back panels.

In addition to straps 13 and 14, straps 17 and 18 are also connected to the body restraint. One end of each strap 17 and 18 is connected as by sewing to each side of the body restraint beneath the respective arm opening 11. Each strap 17 and 18 extends diagonally upward and crosses the other strap, as shown in FIG. 2. The free ends of straps 17 and 18 are adapted to be tied to the head rails 4 of the bed.

The improved body restraint of the invention firmly holds the patient against undesired release, yet permits limited side-to-side movement of the patient. If the patient struggles in an attempt to gain release, the stress on the body restraint will be concentrated under the arm openings due to the diagonal straps 17 and 18. As the front panel 6 is provided with a V-shaped neck 12 there is no possibility of undue stress or pressure being applied to the throat of the patient if the patient should slip down into the restraint during struggling.

Various modes of carrying out the invention are contemplated as being within the scope of the following claims particularly pointing out and distinctly claiming the subject matter which is regarded as the invention.

I claim:

1. A body restraint for a patient, comprising a unitary vest body having a front panel and a pair of back panels and having a neck opening and a pair of arm openings, said front and back panels beng connected together along adjacent side edges with the connections between the front panel and the respective back panels extending the entire distance from the lower edge of said vest body to the respective arm openings, said back panels having adjacent back edges, fastening means for removably fastening said adjacent back edges together, a pair of first reinforcing straps, each first strap attached to the lower edge of a respective back panel and extending transversely across the opposite back panel, strap positioning means mounted on each back panel for positioning the respective first straps to the opposite panels, the free ends of said first straps extending outwardly and being adapted to be connected to an outside object, and a pair of second straps, one end of each second strap being fixedly connected to said vest body immediately beneath the respective arm opening, said second straps extending diagonally upwardly across said back panels in an X-configuration and extending across said fastening means, the opposite end of each second strap being adapted to be connected to an outside object.

2. The body restraint of claim 1, wherein the upper edge of said front panel is recessed downwardly.

3. The body restraint of claim 1, wherein said fastening means comprises a zipper.

* * * * *